United States Patent
Kobayashi et al.

(10) Patent No.: US 9,326,746 B2
(45) Date of Patent: May 3, 2016

(54) X-RAY CT APPARATUS

(71) Applicants: Kabushiki Kaisha Toshiba, Minato-ku (JP); Toshiba Medical Systems Corporation, Otawara-shi (JP)

(72) Inventors: Tadaharu Kobayashi, Otawara (JP); Kenji Mizutani, Nasushiobara (JP); Masanori Matsumoto, Nasushiobara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 92 days.

(21) Appl. No.: 14/467,119

(22) Filed: Aug. 25, 2014

(65) Prior Publication Data
US 2015/0063536 A1   Mar. 5, 2015

(30) Foreign Application Priority Data

Sep. 4, 2013   (JP) .................................. 2013-183098

(51) Int. Cl.
*A61B 6/00* (2006.01)
*A61B 6/03* (2006.01)
*A61B 6/12* (2006.01)

(52) U.S. Cl.
CPC ................. *A61B 6/542* (2013.01); *A61B 6/032* (2013.01); *A61B 6/405* (2013.01); *A61B 6/4417* (2013.01); *A61B 6/4441* (2013.01); *A61B 6/545* (2013.01); *A61B 6/12* (2013.01); *A61B 6/488* (2013.01); *A61B 6/503* (2013.01)

(58) Field of Classification Search
CPC ...... A61B 6/032; A61B 6/405; A61B 6/4417; A61B 6/542; A61B 6/545; A61B 6/4441; A61B 6/12; A61B 6/488; A61B 6/503
USPC ......................................................... 378/4–20
See application file for complete search history.

(56) References Cited

U.S. PATENT DOCUMENTS

2010/0067650 A1* 3/2010 Arai ........................ A61B 6/032
378/16

FOREIGN PATENT DOCUMENTS

JP          2000-152924          6/2000

* cited by examiner

*Primary Examiner* — Courtney Thomas
(74) *Attorney, Agent, or Firm* — Oblon, McClelland, Maier & Neustadt, L.L.P.

(57) ABSTRACT

An X-ray CT apparatus includes a specifying unit, a setting unit, a controller, and a reconstruction unit. The specifying unit refers to exposure dose information to specify a high exposure area in an imaging area in a subject. The setting unit sets a scan condition under which a cross section of the imaging area can be imaged and under which X-rays are not directly applied to the high exposure area or another scan condition under which a cross section of the imaging area can be imaged and under which an X-ray radiation dose directly applied to the high exposure area is reduced relative to an area other than the high exposure area. The controller collects data of X-rays applied from an X-ray tube and detected by an X-ray detector under the set scan condition. The reconstruction unit reconstructs a tomographic image using the collected data of X-rays.

7 Claims, 8 Drawing Sheets

X-RAY CT APPARATUS

CROSS-REFERENCE TO RELATED APPLICATIONS

This application is based upon and claims the benefit of priority from Japanese Patent Application No. 2013-183098, filed on Sep. 4, 2013, the entire contents of all of which are incorporated herein by reference.

FIELD

Embodiments described herein relate generally to an X-ray CT (Computed Tomography) apparatus.

BACKGROUND

X-ray diagnostic apparatuses assist in observation of the positional relation between a blood vessel and a stent or other instrument by an operator such as a doctor (hereinafter referred to as an "operator"), for example, by imaging a subject during intravascular treatment. During such intravascular treatment, the X-ray diagnostic apparatus applies X-rays to a specific site in the subject from a particular direction for a relatively long time.

In this regard, a DTS (Dose Tracking System) manages the X-ray dose that a surface of a subject is exposed to as a skin dose during X-ray imaging by the X-ray diagnostic apparatus. For example, the DTS calculates the exposure dose of the subject based on conditions of radiation by the X-ray diagnostic apparatus. The DTS also generates an artificial human body model based on the subject body information and displays an exposure dose associated with the human body model on a monitor.

Nowadays treatment with an X-ray diagnostic apparatus is sometimes combined with a CT scan with an X-ray CT apparatus. For example, after imaging by an X-ray diagnostic apparatus, an X-ray CT apparatus images the subject and generates a CT image. Although the skin dose by the X-ray diagnostic apparatus is managed by a DTS, the skin dose by the X-ray CT apparatus is not taken into consideration because the X-ray CT apparatus places importance on internal exposure.

DETAILED DESCRIPTION

An X-ray CT apparatus in an embodiment includes a specifying unit, a setting unit, a controller, and a reconstruction unit. The specifying unit refers to exposure dose information that associates a site in a subject radiated with X-rays for taking an X-ray image with a cumulative value of X-ray exposure doses to specify a high exposure area where a cumulative value of exposure doses is equal to or greater than a certain threshold in an imaging area in the subject. The setting unit sets a scan condition under which a cross section of the imaging area can be imaged and under which X-rays are not directly applied to the high exposure area or another scan condition under which a cross section of the imaging area can be imaged and under which an X-ray radiation dose directly applied to the high exposure area is reduced relative to an area other than the high exposure area. The controller rotates a support that supports an X-ray tube for applying X-rays and an X-ray detector for detecting X-rays to collect data of X-rays applied from the X-ray tube and detected by the X-ray detector under the set scan condition. The reconstruction unit reconstructs a tomographic image using the data of X-rays collected under the control of the controller.

An X-ray CT apparatus according to an embodiment will be described below with reference to the drawings.

First Embodiment

Figure 1:
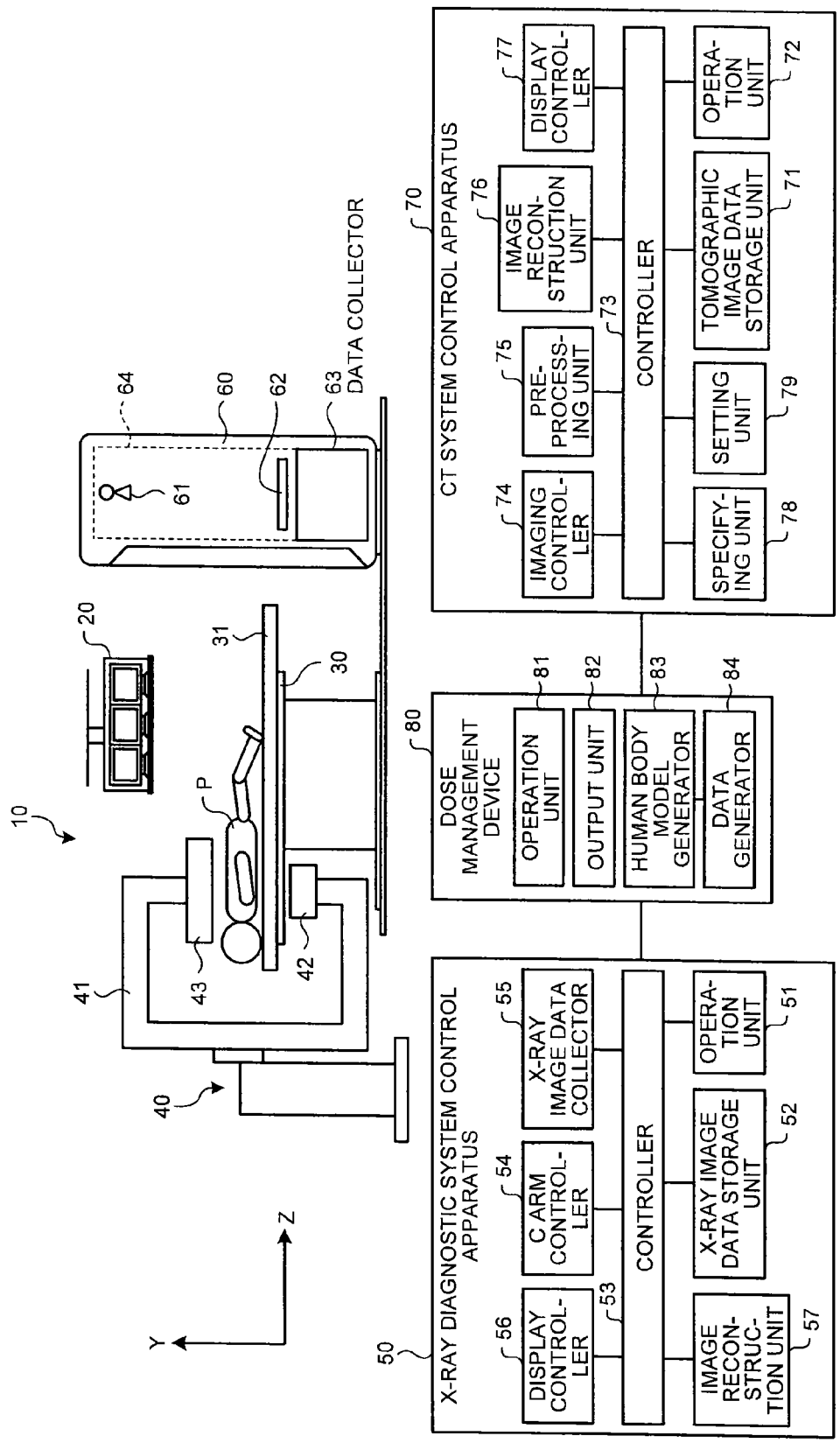
FIG. 1 is a diagram illustrating a configuration example of an X-ray cardiovascular diagnostic system according to a first embodiment.

In the first embodiment, an X-ray cardiovascular diagnostic system 10 will be described as an example of a system having an X-ray CT apparatus. FIG. 1 is a diagram illustrating a configuration example of the X-ray cardiovascular diagnostic system 10 according to the first embodiment. The X-ray cardiovascular diagnostic system 10 according to the first embodiment includes a monitor 20, a couch 30, a dose management device 80, a C arm holder 40, an X-ray diagnostic system control apparatus 50, a CT apparatus gantry 60, and a CT system control apparatus 70. It should be noted that a subject P is not included in the X-ray cardiovascular diagnostic system 10. In the following description, the C arm holder 40 and the X-ray diagnostic system control apparatus 50 may be collectively referred to as an X-ray diagnostic apparatus 200, and the CT apparatus gantry 60 and the CT system control apparatus 70 may be collectively referred to as an X-ray CT apparatus 300.

In this X-ray cardiovascular diagnostic system 10, treatment with the X-ray diagnostic apparatus 200 and a CT scan with the X-ray CT apparatus 300 are combined. For example, an operator such as a doctor (hereinafter referred to as an "operator") gives intravascular intervention treatment with a catheter, for example, while referring to an X-ray image (fluoroscopic image) of a constricted site imaged by the X-ray diagnostic apparatus 200. The operator then, for example, evaluates the effects of the treatment using an X-ray CT image (tomographic image) taken by the X-ray CT apparatus 300. Alternatively, for example, the operator specifies the treatment site using an X-ray CT image (tomographic image) taken by the X-ray CT apparatus 300. The operator then gives intravascular intervention treatment with a catheter while referring to an X-ray image (fluoroscopic image) of a constricted site imaged by the X-ray diagnostic apparatus 200.

Each component of the X-ray cardiovascular diagnostic system 10 will now be described. The monitor 20 displays, for example, an X-ray image such as a fluoroscopic image taken by the X-ray diagnostic apparatus 200 and a tomographic image based on the tomographic image data captured by the X-ray CT apparatus 300. The couch 30 has a couchtop 31 on which a subject P lies, and is movable vertically and horizontally. The couch 30 is capable of moving the couchtop 31 longitudinally or longitudinally and laterally. The couch 30 moves itself or the couchtop 31 to move the subject P to an imaging area of the X-ray diagnostic apparatus 200 and an imaging area of the X-ray CT apparatus 300. In the X-ray cardiovascular diagnostic system 10, the couch 30 is shared between the X-ray diagnostic apparatus 200 and the X-ray CT apparatus 300.

The dose management device 80 manages the dose that the subject P is exposed to in the imaging by the X-ray diagnostic apparatus 200 in terms of a skin dose (exposure dose). For example, the dose management device 80 has an operation unit 81, an output unit 82, a human body model generator 83, and a data generator 84. The dose management device 80 may be called a DTS (Dose Tracking System).

The operation unit 81 accepts a variety of instructions from the operator who manages the dose that the subject P is exposed to. For example, the operation unit 81 accepts from the operator an instruction to display the dose that the subject P is exposed to. Specifically, the operation unit 81 accepts from the operator an instruction to display the dose per minute that the subject P is exposed to. The operation unit 81 accepts from the operator an instruction to display the total dose that the subject P is exposed to during imaging. The output unit 82 is, for example, a monitor for displaying the distribution of exposure dose that is generated by the data generator 84.

The human body model generator 83 generates a human body model of a subject P or a diagnosis target site, based on personal information (gender, age, height, weight, rough body classification, and the like) of the subject P input from the operation unit 81 and/or supplementary information accompanying the X-ray image stored in an X-ray image data storage unit 52. The human body model generator 83 may generate a human body model that approximately represents a subject P or other objects by an ellipse, a sphere, or other shapes or may generate a human body model that faithfully represents a human body or other objects. The human body model generator 83 may generate a whole human body model using the selected profile by automatically selecting a profile closest to a subject P from a plurality of human body cross-sectional profiles, based on the physical information of the subject P. The human body model generator 83 may select a human body model from a plurality of human body models registered in advance in response to an instruction by the operator.

The data generator 84 calculates an exposure dose based on the human body model generated by the human body model generator 83 and the imaging conditions obtained from the X-ray diagnostic apparatus 200 and generates the distribution of exposure dose for a subject P. For example, the data generator 84 generates the distribution of exposure dose by obtaining an exposure dose for each pixel of the human body model, based on the imaging conditions obtained from an X-ray image data collector 55 and a variety of information (SID, the angle between the axis between an X-ray tube 42 and an X-ray detector 43 and the body axis of the subject P or any reference axis, and the like) obtained from the position of an C arm 41 obtained from a C arm controller 54, the position of the couch 30, the position of the X-ray detector 43.

Figure 2:
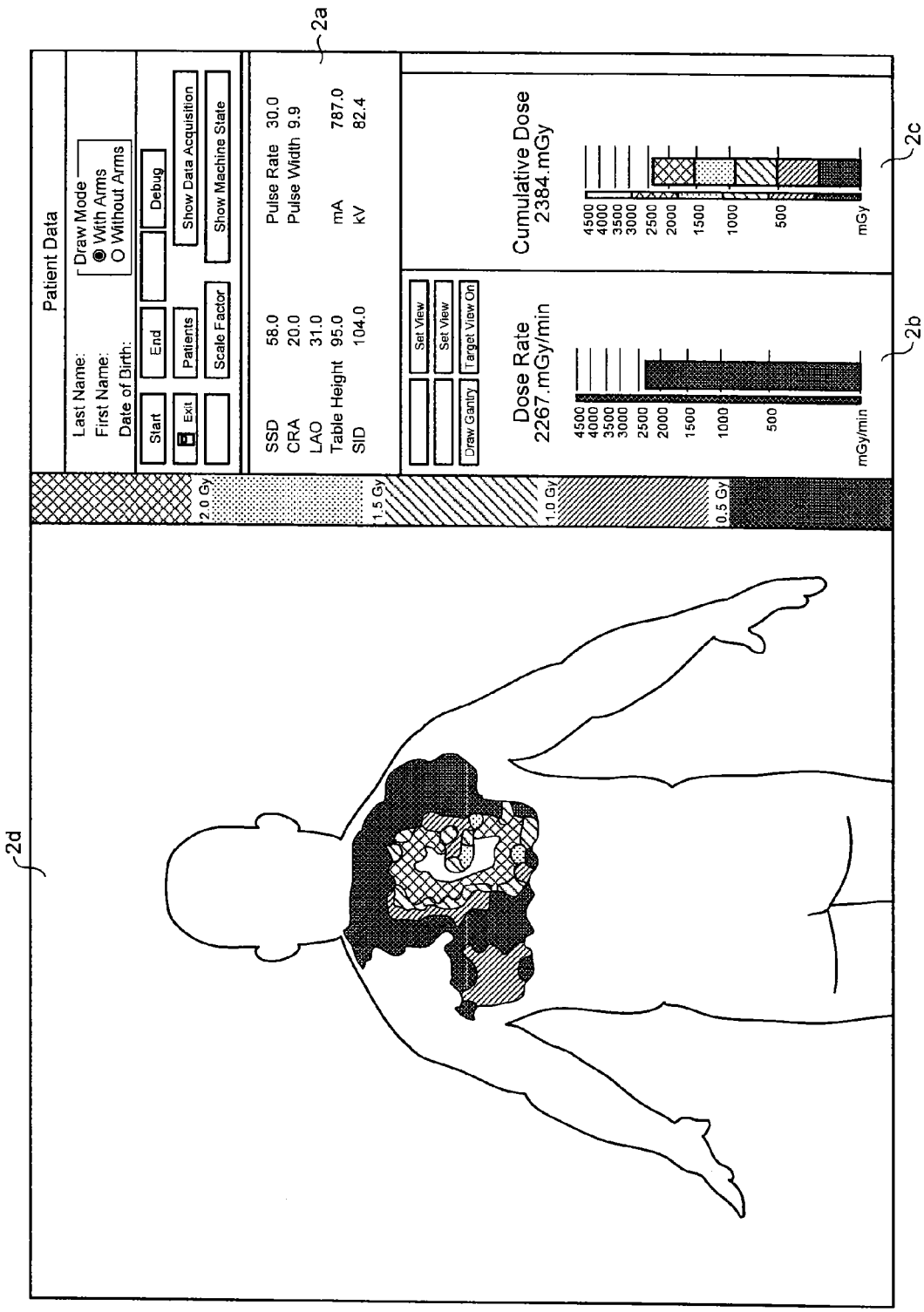
FIG. 2 is a diagram illustrating an example of a screen display for management of exposure doses of a subject P imaged by an X-ray diagnostic apparatus.

A screen display for management of exposure doses of a subject P imaged by the X-ray diagnostic apparatus 200 will be described with reference to FIG. 2. FIG. 2 is a diagram illustrating an example of a screen display for management of exposure doses of a subject P imaged by the X-ray diagnostic apparatus 200. For example, imaging conditions during X-ray image data capturing by the X-ray diagnostic apparatus 200 are displayed in a screen area 2a illustrated in FIG. 2. For example, a value of the exposure dose per minute of the subject P during imaging by the X-ray diagnostic apparatus 200 is displayed in a screen area 2b illustrated in FIG. 2. For example, a value (time-integral value) of the total exposure dose of the subject P during imaging by the X-ray diagnostic apparatus 200 is displayed in a screen area 2c illustrated in FIG. 2.

The dose management device 80 generates information that associates an exposure dose with a site on the human body model and displays the generated information on the monitor 20. Specifically, the dose management device 80 displays image data having color tones assigned in accordance with the exposure doses pixel-by-pixel on the human body model, in a screen area 2d illustrated in FIG. 2. In the following, the information that associates an exposure dose with a site on the human body model is referred to as "exposure dose information". That is, the exposure dose information is associated with a site of a subject using the cumulative value of skin doses of the subject as a cumulative value of X-ray exposure doses.

Returning to FIG. 1, the C arm holder 40 supports the C arm 41. The C arm 41 supports the X-ray tube 42 and the X-ray detector 43 so as to be opposed to each other. The X-ray tube 42 applies X-rays. The X-ray detector 43 detects X-rays applied from the X-ray tube 42 and transmitted through the subject P. The pair of the X-ray tube 42 and the X-ray detector 43 is configured to rotate around the geometric center of rotation.

The X-ray diagnostic system control apparatus 50 controls the C arm holder 40 and collects X-ray image data of the subject P. For example, the X-ray diagnostic system control apparatus 50 includes an operation unit 51, the X-ray image data storage unit 52, a controller 53, the C arm controller 54, the X-ray image data collector 55, a display controller 56, and an image reconstruction unit 57.

The operation unit 51 includes a control panel, a foot switch, and a joy stick and accepts inputs of various operations on the X-ray diagnostic apparatus 200 from the operator. For example, the operation unit 51 accepts from the operator an operation on the couch 30 for moving an observation target in the subject P to the center of the screen. The controller 53 then moves the couch 30 in response to the operation by the operator. The operation unit 51 also accepts an operation of rotating the C arm 41 from the operator. The C arm controller 54 then rotates the C arm 41 in response to the operation by the operator. The operation unit 51 also accepts the settings of imaging conditions from the operator. For example, the operation unit 51 accepts from the operator an operation of setting coronary arteries as an observation target. For example, the operation unit 51 accepts from the operator information such as SID (Source-Isocenter Distance) and FOV (Field of View). The X-ray diagnostic apparatus 200 may retain values of SID, FOV, and the like in advance. The operation unit 51 also accepts an instruction to collect X-ray image data from the operator.

The X-ray image data storage unit 52 stores X-ray image data and other data. The controller 53 controls the entire X-ray diagnostic system control apparatus 50 based on an instruction from the operation unit 51. The C arm controller 54 controls, for example, rotation of the C arm 41 under the control of the X-ray image data collector 55.

The X-ray image data collector 55 accepts an instruction to collect X-ray image data from the operator through the operation unit 51 and then collects X-ray image data by controlling the X-ray tube 42, the X-ray detector 43, and the C arm controller 54. Here, the X-ray image data collector 55 collects an image projected on the X-ray detector 43 by the X-rays applied to the subject P. The X-ray image data collector 55 sends the collected X-ray image data to the display controller 56. The X-ray image data collector 55 also collects image data such as three-dimensional image data. For example, the X-ray image data collector 55 accepts an instruction to collect three-dimensional image data and collects three-dimensional image data by controlling the X-ray tube 42, the X-ray detector 43, and the C arm controller 54. The X-ray image data collector 55 stores the collected three-dimensional image data into the X-ray image data storage unit 52.

The image reconstruction unit 57 generates tomographic image data by performing reconstruction processing such as back projection on the X-ray image data from a plurality of directions obtained by rotating the C arm 41. The image reconstruction unit 57 then stores the reconstructed tomographic image data into the X-ray image data storage unit 52. In the present embodiment, the X-ray diagnostic system control apparatus 50 may be configured without the image reconstruction unit 57.

The display controller 56 allows the monitor 20 to display the X-ray image data collected by the X-ray image data collector 55 and the tomographic image based on the tomographic image data generated by the image reconstruction unit 57.

The CT apparatus gantry 60 contains a rotation frame 64 and a data collector 63. The rotation frame 64 supports an X-ray tube 61 and an X-ray detector 62 described later rotatably around the subject P. The rotation frame 64 is an annular frame that supports the X-ray tube 61 and the X-ray detector 62 opposed to each other with the subject P interposed therebetween and rotates at high speeds on a circular orbit about the subject P.

The X-ray tube 61 generates X-rays based on predetermined tube voltage and tube current applied by a not-illustrated high-voltage generator and rotatably moves around the subject P to apply the X-rays to the subject P lying on the couch 30. The X-ray detector 62 is supported by a pivotable support at a position opposed to the X-ray tube 61 and detects an X-ray dose of X-ray beams transmitted through the subject P. In other words, the X-ray detector 62 detects the intensity of the X-rays transmitted through the subject P. The X-ray detector 62 is configured as a multi-row detector with a plurality of channels and a plurality of rows in which a plurality of X-ray detection channels are arranged in a two-dimensional matrix. The data of the detected transmitted X-ray dose is output to the data collector 63.

The data collector 63 collects data indicating the intensity of the X-rays detected by the X-ray detector 62. The data collector 63 performs processing such as amplification and A/D (Analog to Digital) conversion on the collected data of the transmitted X-ray dose to generate projection data and outputs the generated projection data to the CT system control apparatus 70.

The CT system control apparatus 70 includes a tomographic image data storage unit 71, an operation unit 72, a controller 73, an imaging controller 74, a pre-processing unit 75, an image reconstruction unit 76, a display controller 77, a specifying unit 78, and a setting unit 79. The tomographic image data storage unit 71 stores tomographic image data and other data. The operation unit 72 accepts an input by the operator. For example, the operation unit 72 includes a keyboard and a mouse and outputs a signal for the operator's input to the imaging controller 74. The controller 73 controls the entire CT system control apparatus 70 based on an instruction from the operation unit 72.

The imaging controller 74 controls the operation of each component in the CT apparatus gantry 60. For example, the imaging controller 74 controls the rotating operation of the support, the operation of the X-ray tube 61, the operation of the X-ray detector 62, and the operation of the data collector 63, under a scan condition set by the setting unit 79 described later.

The pre-processing unit 75 performs logarithmic transformation and correction processing such as off-set correction, sensitivity correction, and beam hardening correction on the projection data transmitted from the data collector 63 to generate corrected projection data. The corrected projection data generated by the pre-processing unit 75 is hereinafter referred to as projection data for reconstruction.

The image reconstruction unit 76 performs a process of generating image data and a variety of image processing based on the data collected by the CT apparatus gantry 60. For example, the image reconstruction unit 76 reconstructs the projection data for reconstruction transmitted from the pre-processing unit 75, based on predetermined reconstruction parameters such as a reconstruction area size, a reconstruction matrix size, and a threshold for extracting the site of interest, and generates tomographic image data (X-ray CT image data) of a predetermined number of slices. The image reconstruction unit 76 outputs the tomographic image based on the generated tomographic image data to the display controller 77. The image reconstruction unit 76 also stores the projection data for reconstruction transmitted from the data collector 63 and the generated tomographic image data into the tomographic image data storage unit 71.

The display controller 77 allows the monitor 20 to display a tomographic image based on the tomographic image data generated by the image reconstruction unit 76.

In the X-ray cardiovascular diagnostic system 10 according to the first embodiment with the configuration described above, the X-ray diagnostic apparatus 200 takes an X-ray image (fluoroscopic image) of a constricted site during intravascular intervention treatment with a catheter. The X-ray CT apparatus 300 then, for example, takes a tomographic image of the treatment site subjected to intravascular intervention treatment using the X-ray diagnostic apparatus 200. The conventional X-ray CT apparatus places importance on internal exposure and does not consider the skin dose during capturing of X-ray CT image data. The conventional X-ray CT apparatus therefore applies additional X-rays to an area (high exposure area) where the skin dose from X-rays is high during capturing of X-ray CT image data.

In order to reduce additional X-ray exposure in an area with a high cumulative value of X-ray exposure doses, the X-ray CT apparatus 300 according to the first embodiment performs processing as follows under the control of the specifying unit 78 and the setting unit 79. Specifically, the specifying unit 78 according to the first embodiment refers to exposure dose information that associates a site in a subject P radiated with X-rays for taking an X-ray image with a cumulative value of X-ray exposure doses to specify a high exposure area where a cumulative value of exposure doses is equal to or greater than a certain threshold in an imaging area in the subject P. The setting unit 79 according to the first embodiment then sets a scan condition under which a cross section of the imaging area can be imaged and under which X-rays are not applied to the high exposure area or another scan condition under which a cross section of the imaging area can be imaged and under which an X-ray radiation dose to the high exposure area can be reduced relative to an area other than the high exposure area.

Figure 3:
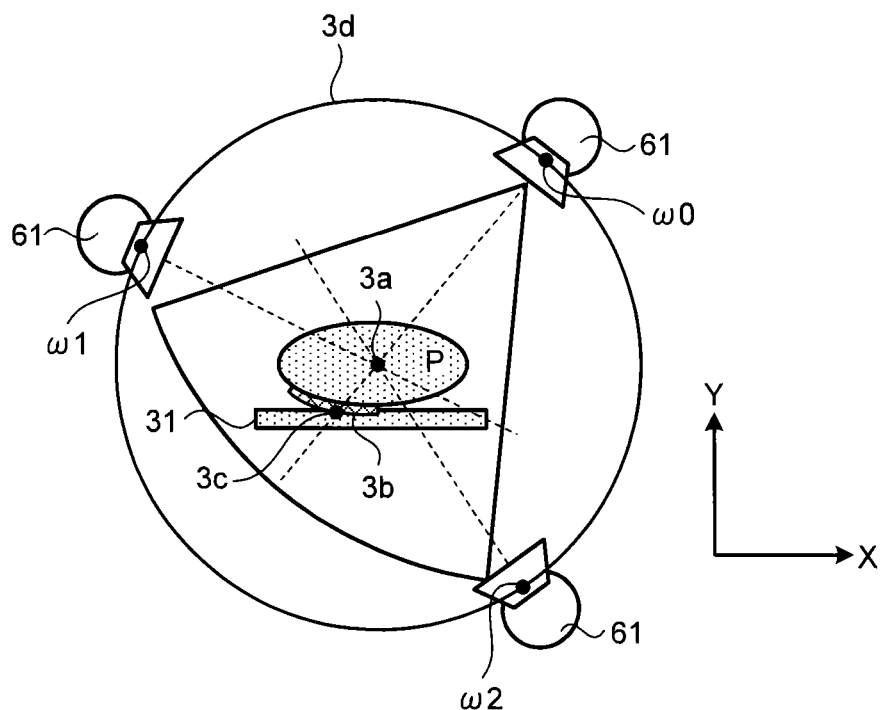
FIG. 3 is a diagram for explaining a scan condition according to the first embodiment.

An example of processing operation of the specifying unit 78 and the setting unit 79 according to the first embodiment will be described below. FIG. 3 is a diagram for explaining a scan condition according to the first embodiment. As illustrated in FIG. 3, a subject P lies on the couchtop 31. In the example illustrated in FIG. 3, the posteroanterior direction of the subject P is represented by the Y-axis direction, and the left-right direction of the subject P is represented by the X-axis direction. The reference sign 3a in FIG. 3 indicates the center of rotation of the rotation frame 64. The X-ray tube 61 applies X-rays to the subject P while rotating on a circular orbit 3d about the center of rotation 3a.

The reference sign 3b in FIG. 3 indicates a high exposure area where the skin dose from X-rays applied by the X-ray diagnostic apparatus 200 is high. The specifying unit 78 according to the first embodiment, for example, acquires exposure dose information from the dose management device 80 and specifies the high exposure area 3b where the cumulative value of exposure doses is equal to or greater than a certain threshold in the imaging area in the subject P. The specifying unit 78 then specifies a center 3c of the high exposure area 3b.

The setting unit 79 according to the first embodiment sets a scan condition under which a cross section of the imaging area can be imaged and under which X-rays are not directly applied to the high exposure area. In other words, the setting unit 79 according to the first embodiment sets a scan condition under which a cross section of the imaging area can be imaged and under which X-rays to be applied to the subject P and not yet transmitted through the subject P are not applied to the high exposure area. For example, the setting unit 79 sets a position opposed to the center 3c on the circular orbit 3d about the center of rotation 3a, as the center (ω0) of a scan range. Here, the angle (rotation angle) of the X-ray tube 61 at which the X-ray tube 61 is located at ω0 is defined as "0 degree (360 degrees)". For convenience of explanation, the clockwise direction about the position at ω0 illustrated in FIG. 3 is called the "+" direction, and the counterclockwise direction about the position at ω0 is called the "−" direction. In the following description, it is assumed that a tomographic image is taken while the X-ray tube 61 rotates in the "+" direction.

The setting unit 79 then sets a scan range of, for example, "180 degrees+fan angle" about ω0. That is, the setting unit 79 sets a scan range for half reconstruction. In the example illustrated in FIG. 3, a scan range is set in which the X-ray tube 61 is rotatably moved from the position at ω1 to the position at ω2.

Figure 4:
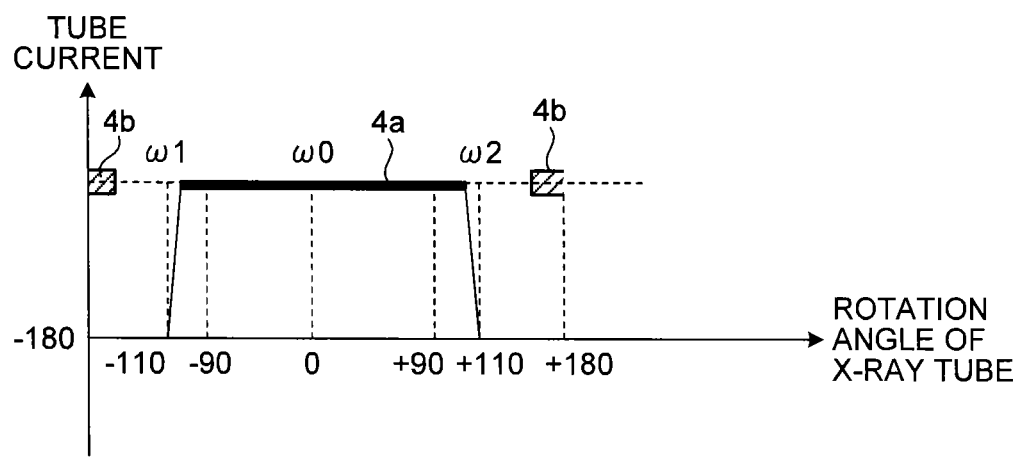
FIG. 4 is a diagram illustrating an example of control on tube current according to the first embodiment.

The setting unit 79 then sets the intensity of tube current in the set scan range. FIG. 4 is a diagram illustrating an example of control on tube current according to the first embodiment. In FIG. 4, the vertical axis represents tube current, and the horizontal axis represents the rotation angle of the X-ray tube 61. For convenience of explanation, it is assumed that the rotation angle of the X-ray tube 61 is the same as the scan range illustrated in FIG. 3. Specifically, the position on the circular orbit 3d that is opposed to the center 3c of the high exposure area 3b illustrated in FIG. 3 is the rotation angle 0 degree. Here, it is assumed that the fan angle is 40 degrees. The setting unit 79 sets a scan condition for performing a half scan with fixed tube current ($I_0$) from the position at −110 degrees to the position at +110 degrees of the rotation angle of the X-ray tube 61.

In the example illustrated in FIG. 4, the range of rotation angles −110 degrees to +110 degrees that is set by the setting unit 79 as a scan range is represented by 4a, and the range of rotation angles corresponding to the high exposure area 3b is represented by 4b. As illustrated in FIG. 4, the setting unit 79 sets 4a corresponding to the rotation angles serving as a scan range for a half scan in the rotation angle range excluding 4b. The setting unit 79 according to the first embodiment may set a scan condition for half reconstruction based on the barycenter of the high exposure area 3b or the point or range set by the operator in the high exposure area 3b as long as the conditions described above are satisfied. That is, the X-ray CT apparatus 300 can reduce additional X-ray radiation to the high exposure area 3b. The image reconstruction unit 76 then performs image reconstruction using the data collected by the CT apparatus gantry 60. The image reconstruction unit 76 may reconstruct single tomographic image data on the X-Y plane or may reconstruct a plurality of tomographic image data along the body axis. The image reconstruction unit 76 may generate a plurality of tomographic image data as single volume data. Although in the foregoing description the position opposed to the center 3c of the high exposure area 3b is set as the center of the scan range, the center of the scan range is not limited to the center 3c of the high exposure area 3b. For example, the setting unit 79 may set a scan range that includes the opposed area located at a position opposed to the high exposure area with the subject interposed therebetween and that allows imaging of a cross section of the imaging area. More specifically, the setting unit 79 may set a scan range for performing a half scan that includes the opposed area located at a position opposed to the high exposure area with the subject interposed therebetween, thereby setting a scan condition under which X-rays are not directly applied to the high exposure area. When the setting unit 79 sets a scan range that includes the opposed area and allows imaging of a cross section of the imaging area, the scan range is not limited to a scan range for performing a half scan.

Figure 5:
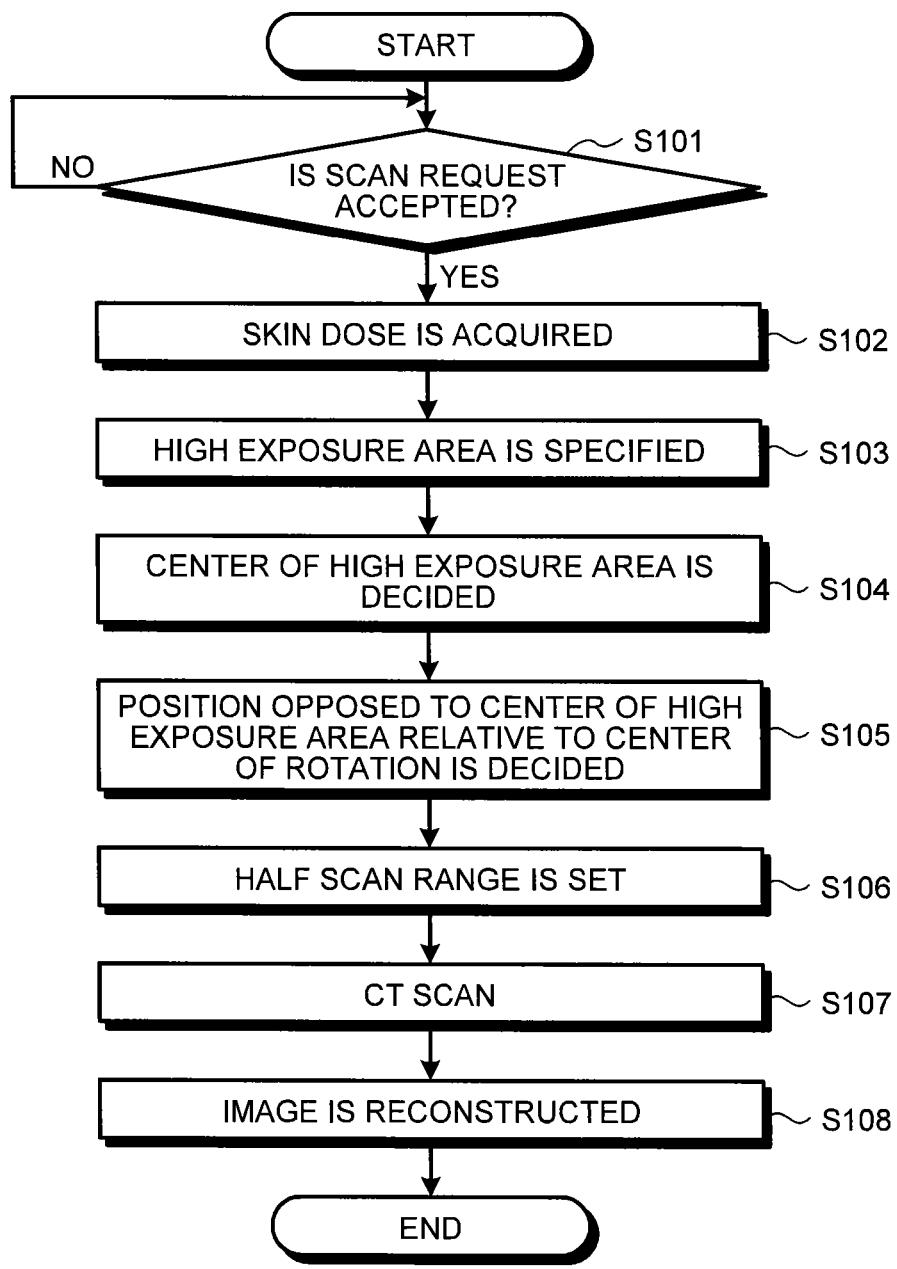
FIG. 5 is a flowchart illustrating the procedure of a process by an X-ray CT apparatus according to the first embodiment.

FIG. 5 is a flowchart illustrating the procedure of a process by the X-ray CT apparatus 300 according to the first embodiment. As illustrated in FIG. 5, the specifying unit 78 determines whether a scan request is accepted (step S101). Here, if the specifying unit 78 determines that a scan request is accepted (Yes at step S101), the exposure dose information is acquired from the dose management device 80 (step S102). If the specifying unit 78 does not determine that a scan request is accepted (No at step S101), the determination process at step S101 is repeated.

The specifying unit 78 then specifies a high exposure area where the skin dose is high, using the acquired exposure dose information (step S103). The specifying unit 78 then decides the center of the specified high exposure area (step S104).

The setting unit 79 decides the position opposed to the center of the high exposure area with respect to the center of rotation of the X-ray CT apparatus 300 (step S105) and sets a half scan range (step S106). The imaging controller 74 controls the operation of the X-ray tube 61, the operation of the X-ray detector 62, and the operation of the data collector 63 so that a CT scan is executed under the scan condition set by the setting unit 79 (step S107). The image reconstruction unit 76 performs image reconstruction using the data collected by the CT apparatus gantry 60 (step S108).

As described above, the X-ray CT apparatus 300 according to the first embodiment refers to exposure dose information that associates a site in a subject P radiated with X-rays for taking an X-ray image with a cumulative value of X-ray exposure doses to specify a high exposure area where a cumulative value of exposure doses is equal to or greater than a certain threshold in an imaging area in the subject P. The X-ray CT apparatus 300 sets a scan condition under which a cross section of the imaging area can be imaged and under which X-rays are not applied to the high exposure area. The X-ray CT apparatus 300 according to the first embodiment thus can reduce additional X-ray exposure in an area where the cumulative value of X-ray exposure doses is high.

Second Embodiment

In the first embodiment, a scan condition for performing half reconstruction is set. The X-ray CT image reconstructed using the X-ray detection data collected under the scan condition for performing half reconstruction has image quality poorer than the X-ray CT image reconstructed under a scan condition for performing full reconstruction. It is therefore preferable that the X-ray CT image be fully reconstructed. However, if full reconstruction is performed, X-rays are also applied to the high exposure area. A second embodiment will now be described in which X-rays are modulated so that the X-ray radiation dose to the high exposure area is reduced.

Figure 6:
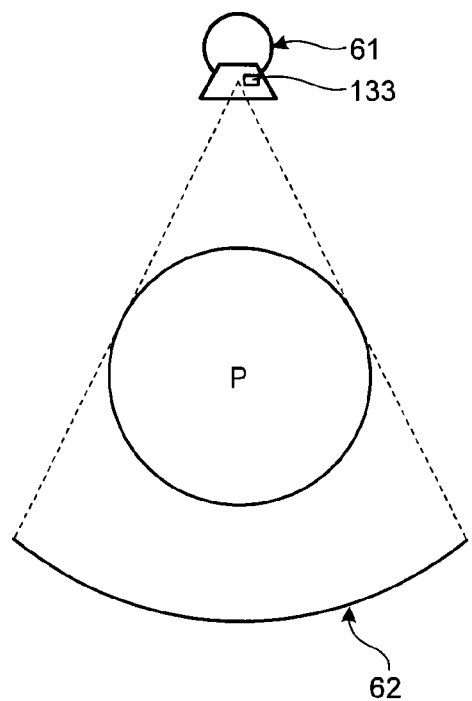
FIG. 6 is a diagram illustrating a reference detector according to a second embodiment.

The configuration of the X-ray cardiovascular diagnostic system 10 according to the second embodiment is similar to the configuration of the X-ray cardiovascular diagnostic system 10 according to the first embodiment. The X-ray CT apparatus 300 according to the second embodiment corrects the effects of modulation of X-ray intensity using a reference detector 133 because X-rays are modulated so that the X-ray radiation dose to the high exposure area is reduced in the second embodiment. The data indicating the intensity of X-rays detected by the reference detector 133 is used to correct variations in X-ray intensity among views (X-ray radiation directions) due to modulation of the intensity of X-rays applied from the X-ray tube 61. FIG. 6 is a diagram illustrating the reference detector 133 installed in the second embodiment.

FIG. 6 is a diagram illustrating the reference detector 133 according to the second embodiment. As illustrated in FIG. 6, in the X-ray CT apparatus 300 according to the second embodiment, the reference detector 133 is provided in the vicinity of the X-ray tube 61 in the CT apparatus gantry 60 to detect the intensity of X-rays immediately after application from the X-ray tube 61. The position where the reference detector 133 is installed is not limited to the vicinity of the X-ray tube 61 and can be changed as desired as long as X-rays are not applied to the subject P or any obstruction and the intensity of X-rays can be detected.

Here, the reference detector 133 outputs data obtained by detecting the intensity of X-rays to the data collector 63 in the same manner as in the X-ray detector 62, and the data collector 63 transmits the detection result from the reference detector 133 as reference data to the CT system control apparatus 70. The pre-processing unit 75 then corrects the projection data captured for each view based on the reference data detected by the reference detector 133 in the corresponding view. Specifically, when the intensity of X-rays is modulated, the pre-processing unit 75 generates projection data from which the effects of modulation of X-ray intensity have been removed (corrected) in all the views. The image reconstruction unit 76 then reconstructs an X-ray CT image by performing back-projection on the projection data for reconstruction generated by the pre-processing unit 75. Although not being detailed in the first embodiment, the X-ray CT apparatus 300 according to the first embodiment has the reference detector 133 and uses the reference detector 133 to correct the intensity of the radiated X-rays, in the same manner as in the X-ray CT apparatus 300 according to the second embodiment.

In the second embodiment with such a configuration, a scan condition for performing full reconstruction is set. The setting of a scan condition for performing full reconstruction in the second embodiment will now be described. The setting unit 79 according to the second embodiment sets a scan condition under which a cross section of the imaging area can be imaged and under which the X-ray radiation dose directly applied to the high exposure area is reduced relative to the area other than the high exposure area. In other words, the setting unit 79 according to the second embodiment sets a scan condition under which a cross section of the imaging area can be imaged and under which the radiation dose to the high exposure area of X-rays not yet transmitted through the subject P is reduced relative to the area other than the high exposure area. For example, the setting unit 79 sets a scan range for performing a full scan and sets a scan condition under which the X-ray radiation dose to the high exposure area is reduced relative to the area other than the high exposure area.

Figure 7:
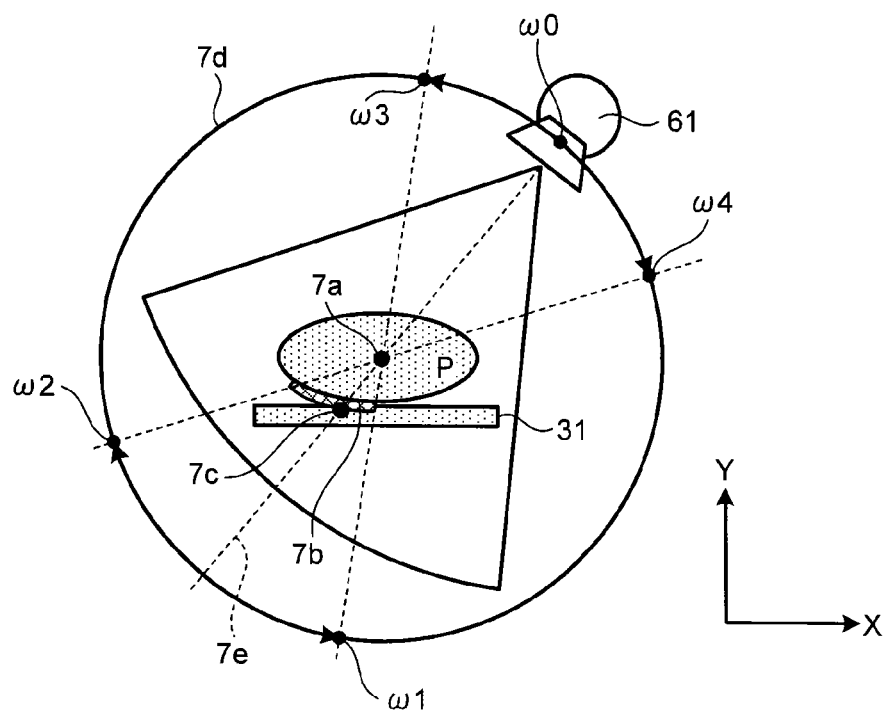
FIG. 7 is a diagram for explaining a scan condition according to the second embodiment.

FIG. 7 is a diagram for explaining a scan condition according to the second embodiment. As illustrated in FIG. 7, a subject P lies on the couchtop 31. In the example illustrated in FIG. 7, the posteroanterior direction of the subject P is represented by the Y-axis direction, and the left-right direction of the subject P is represented by the X-axis direction. The reference sign 7a in FIG. 7 indicates the center of rotation of the rotation frame 64. The X-ray tube 61 applies X-rays to the subject P while rotating on a circular orbit 7d about the center of rotation 7a.

The reference sign 7b in FIG. 7 indicates a high exposure area where the skin dose is high. The specifying unit 78 according to the second embodiment acquires the exposure dose information from the dose management device 80 and specifies the high exposure area 7b. For example, the specifying unit 78 acquires the exposure dose information from the dose management device 80 and specifies the high exposure area 7b where the cumulative value of exposure doses is equal to or greater than a certain threshold in the imaging area in the subject P. The specifying unit 78 then specifies a center 7c of the high exposure area 7b.

The setting unit 79 according to the second embodiment sets a scan range for performing a full scan and sets a scan condition under which the X-ray radiation dose to the high exposure area 7b is reduced relative to the area other than the high exposure area 7b. For example, the setting unit 79 sets a position opposed to the center 7c on the circular orbit 7d about the center of rotation 7a, as the center ($\omega 0$) of the scan range. The reference sign 7e in FIG. 7 indicates the center of radiation range at the position at the rotation angle $\omega 0$.

The setting unit 79 then sets, for example, a scan range of "360 degrees" about $\omega 0$. That is, the setting unit 79 sets a scan range for full reconstruction. In the example illustrated in FIG. 7, the scan range is set in which the X-ray tube 61 is rotatably moved 360 degrees from the position at $\omega 0$.

The setting unit 79 sets a scan condition under which the X-ray radiation dose to the high exposure area is reduced relative to the area other than the high exposure area. For example, the setting unit 79 specifies rotation angles of the X-ray tube 61 in a case where the center of radiation range is located at both ends of the high exposure area. In the example illustrated in FIG. 7, the setting unit 79 specifies $\omega 1$ and $\omega 2$ as the rotation angles of the X-ray tube 61 in a case where the center of radiation range is located at both ends of the high exposure area 7b. The setting unit 79 then sets a condition under which the X-ray radiation dose is reduced in the scan range from the position at the specified rotation angle ω1 to the position at ω2.

The setting unit 79 then specifies a position ω3 opposed to the position at the rotation angle ω1 and a position ω4 opposed to the position at the rotation angle ω2. The setting unit 79 then sets an X-ray radiation dose in the scan range from the position at the rotation angle ω3 to the position at ω4. Here, the setting unit 79 sets a first condition, a second condition, and a third condition as described below as the X-ray radiation dose in the scan range from the position at the rotation angle ω3 to the position at ω4. For example, the setting unit 79 sets as the first condition a condition that X-rays are applied such that the X-ray radiation dose in the scan range from the position at the rotation angle ω3 to the position at ω4 is the same as the radiation dose in a range other than the scan range from the position at the rotation angle ω1 to the position at ω2. Alternatively, the setting unit 79 sets as the second condition a condition that the X-ray radiation dose in the scan range from the position at the rotation angle ω3 to the position at ω4 is reduced in the same manner as in the scan range from the position at the rotation angle ω1 to the position at ω2. Alternatively, the setting unit 79 sets as the third condition a condition that the X-ray radiation dose in the scan range from the position at the rotation angle ω3 to the position at ω4 is further increased relative to a range other than the scan range from the position at the rotation angle ω1 to the position at ω2. The X-ray radiation dose in the full scan range will be described below with reference to FIG. 8 to FIG. 10.

Figure 8:
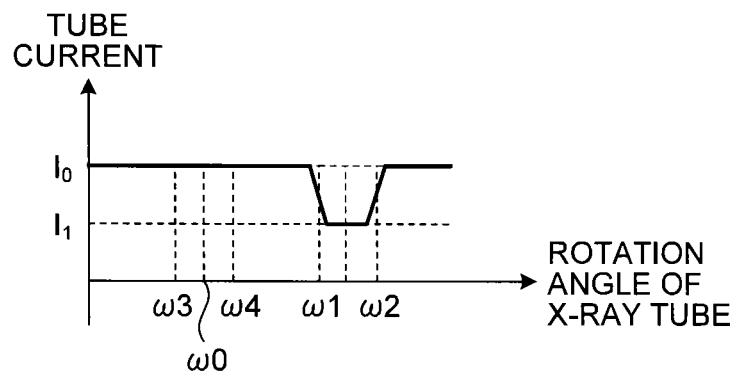
FIGS. 8 to 10 are diagrams illustrating an example of control on tube current according to the second embodiment.
Figure 9:
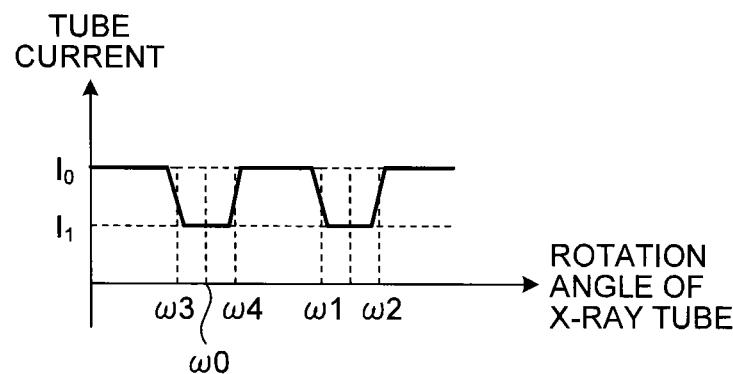
Figure 10:
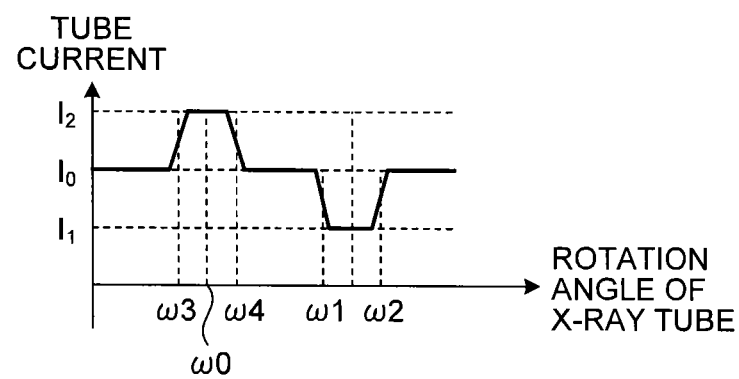

FIG. 8 to FIG. 10 are diagrams illustrating an example of control on tube current according to the second embodiment. In FIG. 8 to FIG. 10, the vertical axis represents tube current, and the horizontal axis represents the rotation angle of the X-ray tube 61. For convenience of explanation, it is assumed that the rotation angle of the X-ray tube 61 is the same as the scan range illustrated in FIG. 7. More specifically, a position on the circular orbit 7d that is opposed to the center 7c of the high exposure area 7b illustrated in FIG. 7 is the rotation angle 0 degree.

FIG. 8 illustrates the first condition. The setting unit 79 sets a condition that the tube current is kept at $I_0$ from the position at the rotation angle ω0 to the position at ω1. The setting unit 79 then sets a condition that the tube current is reduced from $I_0$ to $I_1$ from the position at the rotation angle ω1 to the position at ω2, kept at almost entirely from the position at the rotation angle ω1 to the position at ω2, and thereafter increased from $I_1$ to $I_0$ again. The setting unit 79 then sets a condition that the tube current is kept at $I_0$ from the position at the rotation angle ω2 to the position at ω0.

As described above, the setting unit 79 sets a scan range for performing a full scan and sets a scan condition under which the X-ray radiation dose directly applied to the high exposure area 7b is reduced relative to the area other than the high exposure area. That is, the first condition can reduce additional X-ray radiation to the high exposure area.

FIG. 9 illustrates the second condition. The setting unit 79 sets a condition that the tube current is kept at $I_0$ almost entirely from the position at the rotation angle ω0 to the position at ω4 and thereafter increased from $I_1$ to $I_0$. The setting unit 79 also sets a condition that the tube current is kept at $I_0$ from the position at the rotation angle ω4 to the position at ω1. The setting unit 79 then sets a condition that the tube current is reduced from $I_0$ to $I_1$ from the position at the rotation angle ω1 to the position at ω2, kept at $I_1$ almost entirely from the position at the rotation angle ω1 to the position at ω2, and thereafter increased from $I_1$ to $I_0$ again. The setting unit 79 then sets a condition that the tube current is kept at $I_0$ from the position at the rotation angle ω2 to the position at ω3. The setting unit 79 then sets a condition that the tube current is reduced from $I_0$ to $I_1$ from the position at the rotation angle ω3 to the position at ω0 and thereafter kept at $I_1$ almost entirely from the position at the rotation angle ω3 to the position at ω0.

When X-rays are applied to the area opposed to the high exposure area, the transmitted X-rays cause X-ray exposure in the high exposure area. The second condition is set considering the effects of such transmitted X-rays. That is, in the second condition, the X-ray radiation dose to the area opposed to the high exposure area is also reduced. The setting unit 79 sets a scan condition under which the X-ray radiation dose directly applied to the opposed area located at a position opposed to the high exposure area 7b is reduced relative to the area other than the high exposure area 7b. As a result, the second condition can further reduce additional X-ray radiation to the high exposure area.

FIG. 10 illustrates the third condition. The setting unit 79 sets a condition that the tube current is kept at $I_2$ higher than the tube current $I_0$ almost entirely from the position at the rotation angle ω0 to the position at ω4 and thereafter reduced from $I_2$ to $I_0$ again. The setting unit 79 then sets a condition that the tube current is kept at $I_0$ from the position at the rotation angle ω4 to the position at ω1. The setting unit 79 then sets a condition that the tube current is reduced from $I_0$ to $I_1$ from the position at the rotation angle ω1 to the position at ω2, kept at $I_1$ almost entirely from the position at the rotation angle ω1 to the position at ω2, and thereafter increased from $I_1$ to $I_0$ again. The setting unit 79 then sets a condition that the tube current is kept at $I_0$ from the position at the rotation angle ω2 to the position at ω3. The setting unit 79 then sets a condition that the tube current is increased from $I_0$ to $I_2$ from the position at the rotation angle ω3 to the position at ω0 and thereafter kept at $I_2$ almost entirely from the position at the rotation angle ω3 to the position at ω0.

In the second condition, the image quality is reduced because the X-ray radiation dose to the area opposed to the high exposure area is also reduced. For this reason, in the third condition, the X-ray radiation dose to the area opposed to the high exposure area is increased in order to improve the image quality. More specifically, the setting unit 79 sets a scan condition under which the X-ray radiation dose directly applied to the opposed area located at a position opposed to the high exposure area 7b is increased relative to the area other than the high exposure area 7b. As a result, the third condition can improve the image quality of a tomographic image while reducing additional X-ray radiation to the high exposure area.

The setting unit 79 sets a designated condition, for example, when designation of any one of the first condition, the second condition, and the third condition is accepted from the user. In such a case, the monitor 20 displays selection areas, for example, including a "standard mode" as the first condition, an "exposure dose reduction mode" as the second condition, and an "image quality preference mode" as the third condition. When the user designates one of the selection areas through the operation unit 72, the setting unit 79 sets the condition corresponding to the designated selection area. As described above, the setting unit 79 according to the second embodiment can set a scan condition, in consideration of the trade-off between the exposure dose and the required image quality, based on the judgment by health care providers.

Figure 11:
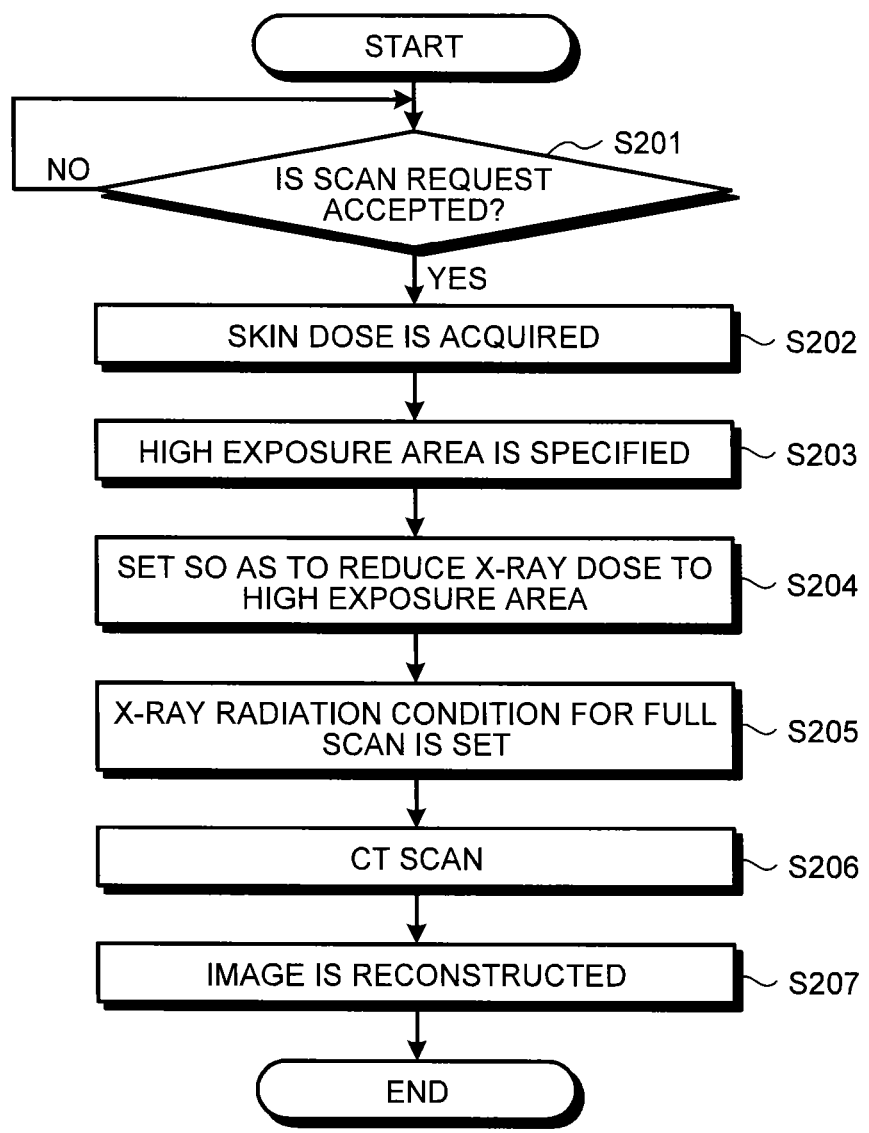
FIG. 11 is a flowchart illustrating the procedure of a process by the X-ray CT apparatus according to the second embodiment.

FIG. 11 is a flowchart illustrating the procedure of a process by the X-ray CT apparatus 300 according to the second embodiment. As illustrated in FIG. 11, the specifying unit 78 determines whether a scan request is accepted (step S201).

Here, if the specifying unit 78 determines that a scan request is accepted (Yes at step S201), the exposure dose information is acquired from the dose management device 80 (step S202). If the specifying unit 78 does not determine that a scan request is accepted (No at step S201), the determination process at step S201 is repeated.

The specifying unit 78 then specifies a high exposure area where the skin dose is high, using the acquired exposure dose information (step S203). The setting unit 79 sets a scan condition so as to reduce the X-ray dose to the specified high exposure area (step S204). The setting unit 79 then sets an X-ray radiation condition in a full scan range (step S205). For example, the setting unit 79 sets any one of the first to third conditions. The imaging controller 74 controls the operation of the X-ray tube 61, the operation of the X-ray detector 62, and the operation of the data collector 63 so that a CT scan is executed under the scan condition set by the setting unit 79 (step S206). The image reconstruction unit 76 performs image reconstruction using the data collected by the CT apparatus gantry 60 (step S207).

As described above, the X-ray CT apparatus 300 according to the second embodiment sets a scan range for performing a full scan and sets a scan condition under which the X-ray radiation dose to the high exposure area is reduced relative to the area other than the high exposure area. The X-ray CT apparatus 300 according to the second embodiment thus can reduce the X-ray radiation dose to the area of the subject P where the cumulative value of exposure doses is high.

The X-ray CT apparatus 300 according to the second embodiment sets the first condition, the second condition, or the third condition as the X-ray radiation dose applied to the area opposed to the high exposure area. For example, the X-ray CT apparatus 300 according to the second embodiment sets as the second condition a scan condition under which the X-ray radiation dose to the opposed area located at a position opposed to the high exposure area is reduced relative to the area other than the high exposure area. The X-ray CT apparatus 300 according to the second embodiment thus can further reduce the X-ray radiation to the high exposure area.

For example, the X-ray CT apparatus 300 according to the second embodiment sets as the third condition a scan condition under which the X-ray radiation dose to the opposed area located at a position opposed to the high exposure area is increased relative to the area other than the high exposure area. The X-ray CT apparatus 300 according to the second embodiment thus can improve the image quality of a tomographic image while reducing the X-ray radiation to the high exposure area.

In the foregoing description, the setting unit 79 sets a designated condition, for example, when designation of any one of the first condition, the second condition, and the third condition is accepted from the user. However, embodiments are not limited thereto. For example, the setting unit 79 may automatically set the selection of the first condition, the second condition, or the third condition in accordance with the exposure dose in the high exposure area. Here, when the threshold for use in determination as to a high exposure area is a "first threshold", the setting unit 79 sets a "second threshold" having a value greater than the first threshold and a "third threshold" having a value greater than the second threshold for the exposure dose in the high exposure area. The setting unit 79 then sets the third condition as a scan condition when the exposure dose in the high exposure area is equal to or greater than the first threshold and smaller than the second threshold. The setting unit 79 sets the first condition as a scan condition when the exposure dose in the high exposure area is equal to or greater than the second threshold and smaller than the third threshold. The setting unit 79 sets the second condition as a scan condition when the exposure dose in the high exposure area is equal to or greater than the third threshold. As described above, the setting unit 79 according to the second embodiment can set a scan condition as appropriate from the first condition, the second condition, and the third condition in accordance with the exposure dose in the high exposure area.

Third Embodiment

In the foregoing embodiments, a scan condition for performing half reconstruction or full reconstruction is set, for example, when the X-ray CT apparatus 300 images a cross section of the treatment site subjected to intravascular intervention treatment using the X-ray diagnostic apparatus 200. The X-ray diagnostic apparatus 200, however, can generate three-dimensional data by rotating the C arm 41. The description given in the first embodiment and the second embodiment is therefore applicable to the X-ray diagnostic apparatus 200.

Specifically, the X-ray diagnostic apparatus 200 may set a scan condition for taking a tomographic image so as to reduce the X-ray radiation dose to the high exposure area. A third embodiment will now be described in which the X-ray diagnostic apparatus 200 sets a scan condition so as to reduce the X-ray radiation dose to the high exposure area.

Figure 12:
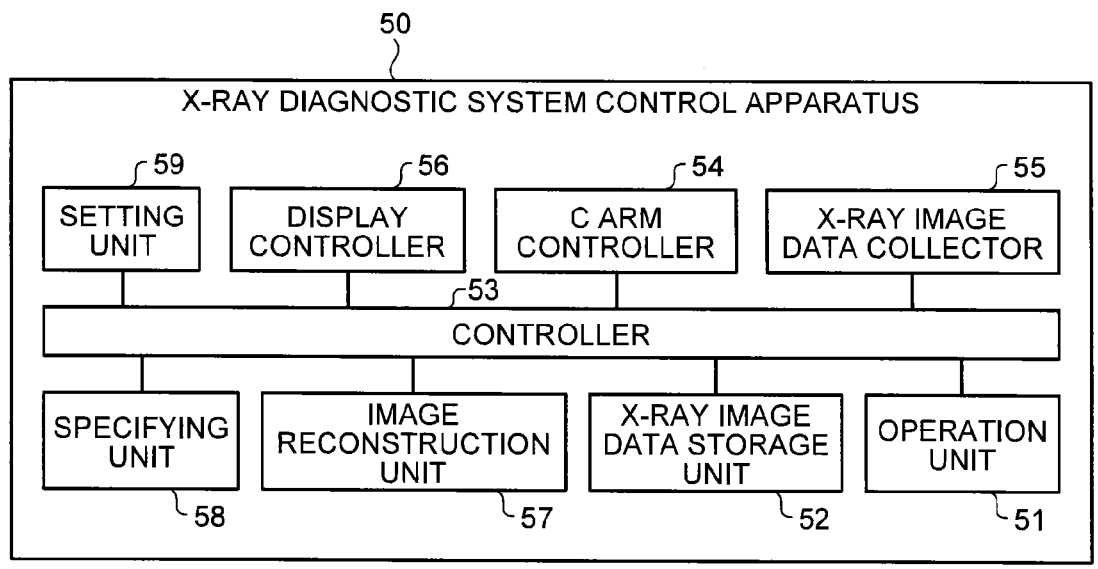
FIG. 12 is a diagram illustrating a configuration example of an X-ray diagnostic system control apparatus according to a third embodiment.

The configuration of the X-ray cardiovascular diagnostic system 10 according to the third embodiment is the same as the configuration of the X-ray cardiovascular diagnostic system 10 according to the first embodiment except that the configuration of the X-ray diagnostic system control apparatus 50 is different. FIG. 12 is a diagram illustrating a configuration example of the X-ray diagnostic system control apparatus 50 according to the third embodiment. As illustrated in FIG. 12, the X-ray diagnostic system control apparatus 50 according to the third embodiment includes an operation unit 51, an X-ray image data storage unit 52, a controller 53, a C arm controller 54, an X-ray image data collector 55, a display controller 56, an image reconstruction unit 57, a specifying unit 58, and a setting unit 59. The functions of the specifying unit 58 are the same as the functions of the specifying unit 78 according to the first embodiment, and the functions of the setting unit 59 are the same as the functions of the setting unit 79 according to the first embodiment.

Figure 13:
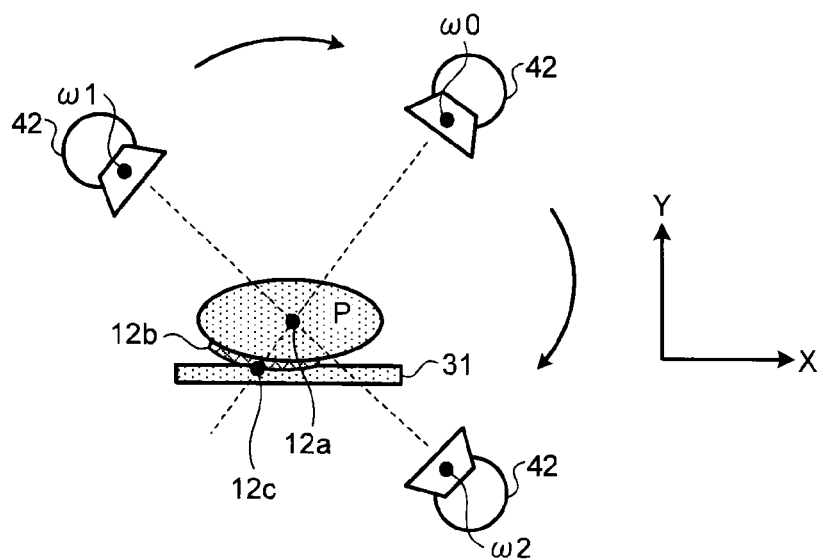
FIG. 13 is a diagram for explaining a scan condition according to the third embodiment.

FIG. 13 is a diagram for explaining a scan condition according to the third embodiment. As illustrated in FIG. 13, a subject P lies on the couchtop 31. In the example illustrated in FIG. 13, the posteroanterior direction of the subject P is represented by the Y-axis direction, and the left-right direction of the subject P is represented by the X-axis direction. The reference sign 12a in FIG. 13 indicates the center of rotation of the C arm 41. The X-ray tube 42 applies X-rays to the subject P while rotating on a circular orbit about the center of rotation 12a.

The reference sign 12b in FIG. 13 indicates a high exposure area that is an area where the skin dose from X-rays applied by the X-ray diagnostic apparatus 200 is high. The specifying unit 58 according to the third embodiment, for example, acquires exposure dose information from the dose management device 80 and specifies the high exposure area 12b where the cumulative value of exposure doses is equal to or greater than a certain threshold in the imaging area in the subject P. The specifying unit 58 then specifies a center 12c of the high exposure area 12b. The specifying unit 58 may specify the barycenter of the high exposure area 12b. Alternatively, the specifying unit 58 may use the point set by the operator in the human body model, as the center or barycenter.

The setting unit 59 according to the third embodiment sets a scan condition under which a cross section of the imaging area can be imaged and under which X-rays are not directly applied to the high exposure area. In other words, the setting unit 59 according to the third embodiment sets a scan condition under which a cross section of the imaging area can be imaged and under which X-rays to be applied to the subject P and not yet transmitted through the subject P are not applied to the high exposure area. For example, the setting unit 59 sets a position opposed to the center 12c on the circular orbit about the center of rotation 12a, as the center ($\omega 0$) of the scan range. Here, the angle (rotation angle) of the X-ray tube 42 at which the X-ray tube 42 is located at $\omega 0$ is defined as "0 degree (360 degrees)". For convenience of explanation, the clockwise direction about the position at $\omega 0$ illustrated in FIG. 13 is called the "+" direction, and the counterclockwise direction about the position at $\omega 0$ is called the "−" direction. In the following description, it is assumed that the X-ray tube 42 takes a tomographic image while rotating in the "+" direction.

The setting unit 59 then sets a scan range of "180 degrees" about $\omega 0$. That is, the setting unit 59 sets a scan range for half reconstruction. In the example illustrated in FIG. 13, the scan range is set in which the X-ray tube 42 is rotatably moved from the position at $\omega 1$ to the position at $\omega 2$. With this setting of the scan range, the X-ray diagnostic apparatus 200 according to the third embodiment can reduce the X-ray radiation dose to the high exposure area.

In the foregoing description of the third embodiment, a scan condition for performing half reconstruction is set on the premise that the C arm 41 is not capable of 360-degree rotation. However, if the C arm 41 is capable of 360-degree rotation, a scan condition for performing full reconstruction may be set in the same manner as described in the second embodiment. In such a case, the setting unit 59 sets a scan condition in which the X-ray radiation dose to the high exposure area is reduced. That is, the setting unit 59 sets the X-ray radiation dose to the area opposed to the high exposure area by selecting one from the first to third conditions as appropriate, depending on the exposure dose and the requested image quality, in the same manner as in the second embodiment.

Other Embodiments

In the foregoing description of the first to third embodiments, a scan condition is set with reference to a high exposure area in the X-ray cardiovascular diagnostic system 10 having the X-ray diagnostic apparatus 200 and the X-ray CT apparatus 300. However, the setting of a scan condition described in the foregoing first to third embodiments is applicable when the X-ray diagnostic apparatus 200 is used alone or when the X-ray CT apparatus 300 is used alone.

When there are a plurality of high exposure areas, the setting unit 59 and the setting unit 79 may set a scan condition in which the X-ray radiation dose is reduced for each high exposure area. When full reconstruction is performed, the setting unit 59 and the setting unit 79 may further set the X-ray radiation dose to the area opposed to the high exposure area, for each high exposure area, by selecting one of the first to third conditions as appropriate depending on the exposure dose and the requested image quality, in the same manner as in the second embodiment.

The dose management device 80 may include the specifying unit 78 and the setting unit 79. In such a case, the dose management device 80 acquires information indicating whether the reconstruction condition is half reconstruction or full reconstruction from an external device (for example, the X-ray diagnostic apparatus, the X-ray CT apparatus, or an image server apparatus) connected through a network such as a LAN (Local Area Network). The dose management device 80 then sets a scan condition in accordance with the reconstruction condition and notifies the external device of the set condition. The external device thus can reduce additional X-ray exposure in the high exposure area.

The illustrated components are functional concepts and are not necessarily physically configured as illustrated in the drawings. For example, the X-ray diagnostic apparatus 200 and the dose management device 80 may be integrated as an X-ray diagnostic apparatus.

The whole or any part of the processing functions performed in each component may be implemented by a CPU and a program analyzed and executed by the CPU or may be implemented as hardware with wired logic.

At least one of the embodiments described above can reduce additional X-ray exposure in an area where the cumulative value of X-ray exposure doses is high.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
  a specifying unit configured to refer to exposure dose information that associates a site in a subject radiated with X-rays for taking an X-ray image with a cumulative value of X-ray exposure doses to specify a high exposure area where a cumulative value of exposure doses is equal to or greater than a certain threshold in an imaging area in the subject;
  a setting unit configured to set a scan condition that allows imaging of a cross section of the imaging area and under which X-rays are not directly applied to the high exposure area or another scan condition that allows imaging of a cross section of the imaging area and under which an X-ray radiation dose directly applied to the high exposure area is reduced relative to an area other than the high exposure area;
  a controller configured to rotate a support that supports an X-ray tube for applying X-rays and an X-ray detector for detecting X-rays to collect data of X-rays applied from the X-ray tube and detected by the X-ray detector under the set scan condition; and
  a reconstruction unit configured to reconstruct a tomographic image using the data of X-rays collected under control of the controller.

2. The X-ray CT apparatus according to claim 1, wherein the X-ray image is generated by an X-ray diagnostic apparatus, and
  the exposure dose information is associated with the site in the subject using a cumulative value of skin doses of the subject as the cumulative value of X-ray exposure doses.

3. The X-ray CT apparatus according to claim 1, wherein the setting unit sets a scan range that includes an opposed area located at a position opposed to the high exposure area with the subject interposed therebetween and that allows imaging of a cross section of the imaging area.

4. The X-ray CT apparatus according to claim 1, wherein the setting unit sets a scan range for performing a half scan that includes an opposed area located at a position opposed to the high exposure area with the subject interposed therebetween, thereby setting a scan condition under which X-rays are not directly applied to the high exposure area.

5. The X-ray CT apparatus according to claim 1, wherein the setting unit sets a scan range for performing a full scan and sets the scan condition under which an X-ray radiation dose directly applied to the high exposure area is reduced relative to an area other than the high exposure area.

6. The X-ray CT apparatus according to claim 5, wherein the setting unit further sets the scan condition under which an X-ray radiation dose directly applied to an opposed area located at a position opposed to the high exposure area is reduced relative to an area other than the high exposure area.

7. The X-ray CT apparatus according to claim 5, wherein the setting unit further sets the scan condition under which an X-ray radiation dose directly applied to an opposed area located at a position opposed to the high exposure area is increased relative to an area other than the high exposure area.

\* \* \* \* \*